US006665191B2

United States Patent
Blood et al.

(10) Patent No.: US 6,665,191 B2
(45) Date of Patent: Dec. 16, 2003

(54) MULTI-FOLDED PRINTED WIRING CONSTRUCTION FOR AN IMPLANTABLE MEDICAL DEVICE

(75) Inventors: James E. Blood, Shoreview, MN (US); Moira B. Sweeney, St Paul, MN (US); Michael J. Kane, Lawrenceville, GA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 64 days.

(21) Appl. No.: 09/949,910

(22) Filed: Sep. 10, 2001

(65) Prior Publication Data

US 2003/0048621 A1 Mar. 13, 2003

(51) Int. Cl.$^7$ .................................................. H05K 1/14
(52) U.S. Cl. ........................ 361/749; 361/784; 361/796; 361/818; 174/254
(58) Field of Search ................................. 361/749–751, 361/784, 796, 803, 818; 439/493; 174/254; 324/754, 765; 257/723, 724; 600/374; 607/4, 5, 9, 119, 152

(56) References Cited

U.S. PATENT DOCUMENTS

| | | | |
|---|---|---|---|
| 4,495,546 A | * | 1/1985 | Nakamura et al. ........... 361/749 |
| 4,639,556 A | | 1/1987 | Hartl et al. |
| 4,675,785 A | | 6/1987 | Young |
| 4,923,735 A | | 5/1990 | Peerlkamp |
| 4,928,206 A | * | 5/1990 | Porter et al. ................ 361/699 |
| 5,121,297 A | | 6/1992 | Haas |
| 5,162,140 A | | 11/1992 | Taniguchi |
| 5,204,806 A | * | 4/1993 | Sasaki et al. ................ 361/749 |
| 5,212,218 A | | 5/1993 | Rinehart |
| 5,258,094 A | | 11/1993 | Furui et al. |
| 5,266,746 A | | 11/1993 | Nishihara et al. |
| 5,313,416 A | * | 5/1994 | Kimura ........................ 365/52 |
| 5,345,205 A | * | 9/1994 | Kornrumpf .................. 333/246 |
| 5,398,163 A | | 3/1995 | Sano |
| 5,448,511 A | * | 9/1995 | Paurus et al. .................. 365/52 |
| 5,709,805 A | | 1/1998 | Davis et al. |
| 5,717,556 A | * | 2/1998 | Yanagida ..................... 361/803 |
| 5,727,310 A | | 3/1998 | Casson et al. |
| 5,800,650 A | | 9/1998 | Anderson et al. |
| 5,834,704 A | | 11/1998 | Tanaka |
| 5,917,149 A | | 6/1999 | Barcley et al. |
| 5,917,158 A | | 6/1999 | Takao et al. |
| 5,924,873 A | | 7/1999 | Barcley et al. |
| 5,949,657 A | | 9/1999 | Karabatsos |
| 5,976,391 A | | 11/1999 | Belke, Jr. et al. |
| 5,981,870 A | | 11/1999 | Barcley et al. |
| 6,016,253 A | * | 1/2000 | Seitz et al. .................. 361/735 |
| 6,410,983 B1 | * | 6/2002 | Moriizumi et al. ......... 257/723 |

* cited by examiner

*Primary Examiner*—John B. Vigushin
(74) *Attorney, Agent, or Firm*—Nikolai & Mersereau, P.A.; Thomas J. Nikolai

(57) ABSTRACT

A printed circuit assembly for use in an implantable medical device comprises a plurality of panels having active and passive circuit components on one major surface thereof, the plurality of panels being interconnected with flexible flat cable segments allowing the assembly to be folded so as to place the individual panels carrying the circuit components in a stacked relationship. By providing conductive layers on predetermined surfaces of the panels, shielding is provided to inhibit noise generating circuitry from contaminating wanted signals passing between the components and the plural panels.

10 Claims, 5 Drawing Sheets

MULTI-FOLDED PRINTED WIRING CONSTRUCTION FOR AN IMPLANTABLE MEDICAL DEVICE

BACKGROUND OF THE INVENTION

I. Field of the Invention

This invention relates generally to implantable electronic tissue stimulating devices, and more particularly to the physical packaging of the electronic circuitry used in such devices in which circuit boards carrying hybrid circuitry are interconnected with flexible printed conductors, allowing the boards to be juxtaposed by folding the flexible interconnecting conductors.

II. Discussion of the Prior Art

The miniaturization of electronic devices has resulted in a widespread use of flexible printed circuit boards and interconnecting cabling. The use of flexible printed circuitry can minimize the space required to accommodate interconnected electronic circuits. The printed circuit boards are usually fitted into an hermetically sealed, moisture-impervious housing of such devices as pacemakers, defibrillators, neurostimulators, hearing aids and other small electronic devices. Typically, limits are imposed on the construction of the flexible printed circuit boards because of volume restrictions imposed by the allowable size of the housing of the implantable device in which the circuitry is contained.

Taking as an example a small electronic device, such as an implantable defibrillator, it typically requires a hybrid circuit including discrete and integrated circuit components that must be connected to and contained within a hermetically sealed housing with a battery power supply and energy storage capacitors. In prior art designs, the hybrid circuit is typically disposed on a multi-layer circuit board with active and passive circuit components mounted on the opposed major surfaces of the printed circuit board. While this approach generally permits an increased component count-per-unit volume occupied, it tends to increase the cost of manufacture in that multiple passes with pick-and-place machines are needed to populate both sides of the printed circuit boards with components.

It is known in the art to provide multiple printed circuit boards interconnected with one another by flexible conductors embedded in insulation layers that can also be flexed. See, for example, the Haas Patent 5,121,297. There is no teaching in this patent, however, of having the substrates on which circuit components are mounted in other than a coplanar relationship.

The Karabatsos Patent 5,949,657 describes an electronic assembly comprising a number of rigid substrates or panels that are connected by flexible wired jumpers, allowing the multiple boards to be folded so as to be non-coplanar. The '657 patent does not address problems brought about by close proximity of circuit components upon the folding of the assembly as far as EMI is concerned.

Thus, a need exists for a printed circuit assembly that allows for a relatively high component density, the ability to populate the printed circuit panels with components using only a single pass with automated pick-and-place equipment and which incorporates requisite shielding to prevent noise-generating circuits from adversely affecting operation of other components comprising the overall circuit assembly. The present invention meets these needs and provides other advantages and improvements that will be evident to those skilled in the art upon review of the following description and drawings.

SUMMARY OF THE INVENTION

The present invention provides a packaging approach that utilizes a plurality of printed circuit panels interconnected by flexible interconnecting flat cabling so that components may be mounted on one major surface of the panels only. Thus, only a single pass with pick-and-place equipment is require to populate the panels which then may be juxtaposed in non-coplanar relationship by folding the flexible interconnecting cabling. During initial component layout, consideration is given to component placement so that noise-generating components will not be closely proximate other components that may be sensitive to such noise following the folding thereof. Further, by including conductive shield structures in the printed circuit board, and by folding the assembly so that the components face outward, the shielding layers will be interdispersed with the active and passive components, thereby further reducing radio frequency interference and noise. The configuration also allows for the direct connection of ancillary components, such as batteries and capacitors, thereby reducing the inter-complexity and the cost of manufacture.

BRIEF DESCRIPTION OF THE DRAWINGS

The foregoing features, objects and advantages of the invention will become apparent to those skilled in the art from the following detailed description from the preferred embodiment, especially when considered in conjunction with the accompanying drawings in which like numerals in the several views refer to corresponding parts.

DESCRIPTION OF THE PREFERRED EMBODIMENT

The present invention is applicable to a variety of medical devices utilizing active and passive hybrid circuit components. The invention will be described generally in the context of a printed circuit board assembly for an implantable cardiac rhythm management device, but it is to be understood that the invention may find utility in other product areas as well.

Figure 1:
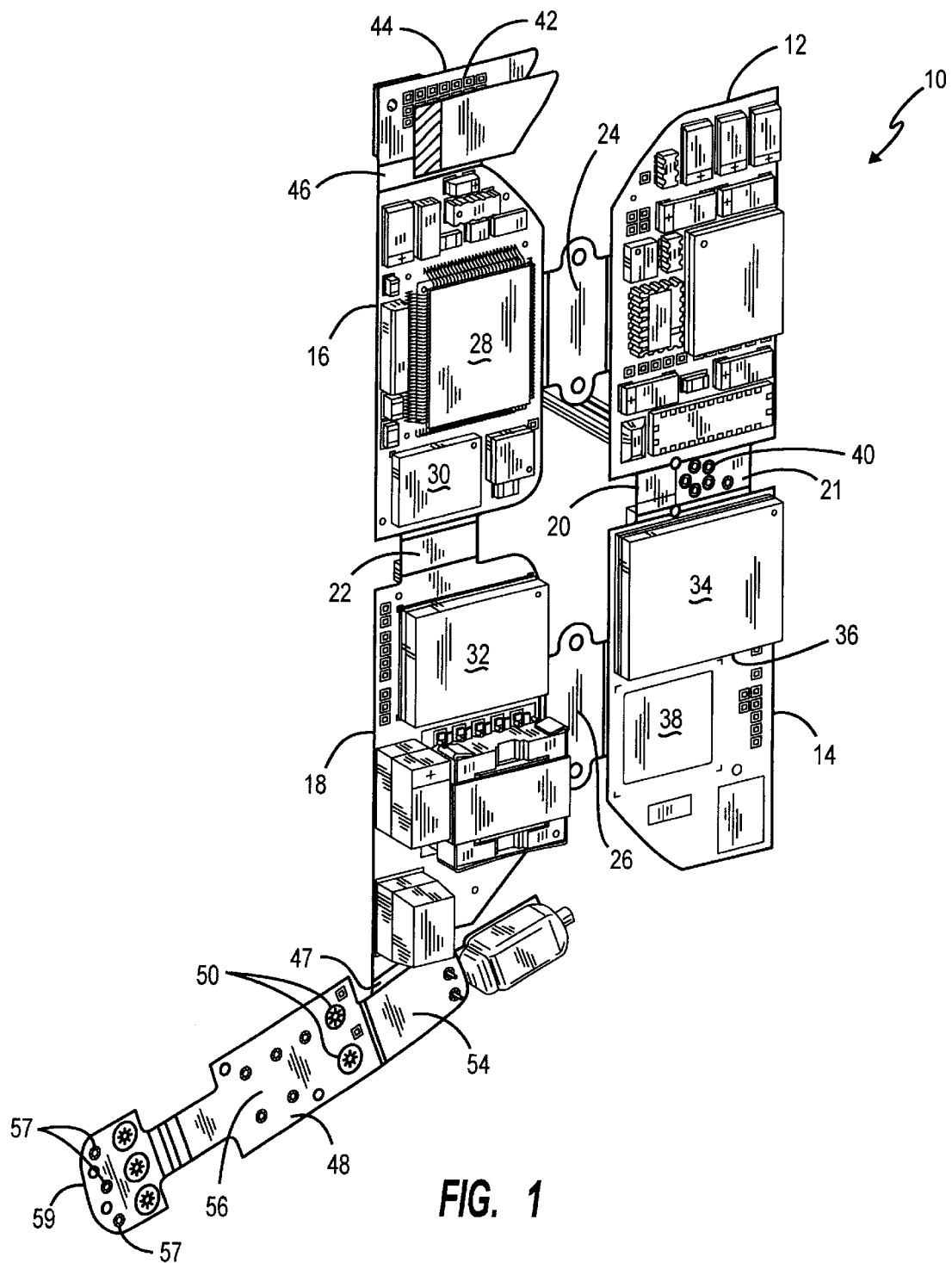
FIG. 1 is a front isometric view of a circuit assembly constructed in accordance with the present invention in an unfolded state.

The printed circuit assembly in FIG. 1 is indicated generally by numeral 10 and is illustrated as including four discrete printed circuit boards or panels 12, 14, 16 and 18 arranged in a 2×2 matrix that are interconnected with one another by means of flat, flexible printed cabling segments. More particularly, panel 12 is connected to panel 14 by a flexible flat printed conductor cable segment 20 and printed circuit panel 16 is joined to printed circuit panel 18 by flexible flat cable segment 22. Printed circuit panel 12 is joined to printed circuit panel 16 using a flat conductor cable segment 24 and printed circuit panel 14 is joined to printed circuit panel 18 via flat conductor cable segment 26.

As is further seen in FIG. 1, each of the printed circuit panels is populated on one major surface only with hybrid circuitry including integrated circuit chips 28 and 30 on panel 16 as well as discrete components including resistors, diodes, capacitors also located on the panel 16. In a similar fashion, printed circuit panel 18 has mounted thereon a multi-chip module 32 and other electronic components as illustrated. Because the components are disposed only on one major surface, automated pick-and-place equipment is only required to make a single pass to fully populate the several interconnected panels.

Printed circuit panel 14 has a plastic surface mount multi-chip module which is connected by printed wiring to other points in the assembly. A portion of the printed circuit panel 14 includes a copper substrate that functions as a shield inhibiting EMI from adversely interfering with signals being developed and conducted between circuit components.

A plurality of input and output tie points are located on the flat cable conductor segment 21 and are identified by numeral 40. These tie points are adapted to be connected to feed-through pins 41 (FIG. 4) that are conventionally used to connect lead terminal contacts in the molded plastic header portion of a pacemaker or defibrillator to the electronic circuit 10 contained within the hermetically sealed housing or can of the device.

The assembly includes a plurality of circuit test point terminals scattered through. For example, test points 42 are disposed on a small printed circuit panel 44 that connects to the printed circuit panel 16 by a flexible cable segment 46 and that can be folded in. Before the circuitry 10 is placed within its housing, test probes may be applied to the test points 42 to ensure that the circuitry is properly operating.

Flex circuitry 47 is also used to join a printed circuit panel 48 to the printed circuit panel 18. The printed circuit panel 48 includes a plurality of contacts, as at 57, that are adapted to connect to the energy storage capacitors utilized in implantable defibrillator circuits. Further contacts 50 on a panel 48 are adapted to connect to a battery (not shown) used to power the device.

Figure 2:
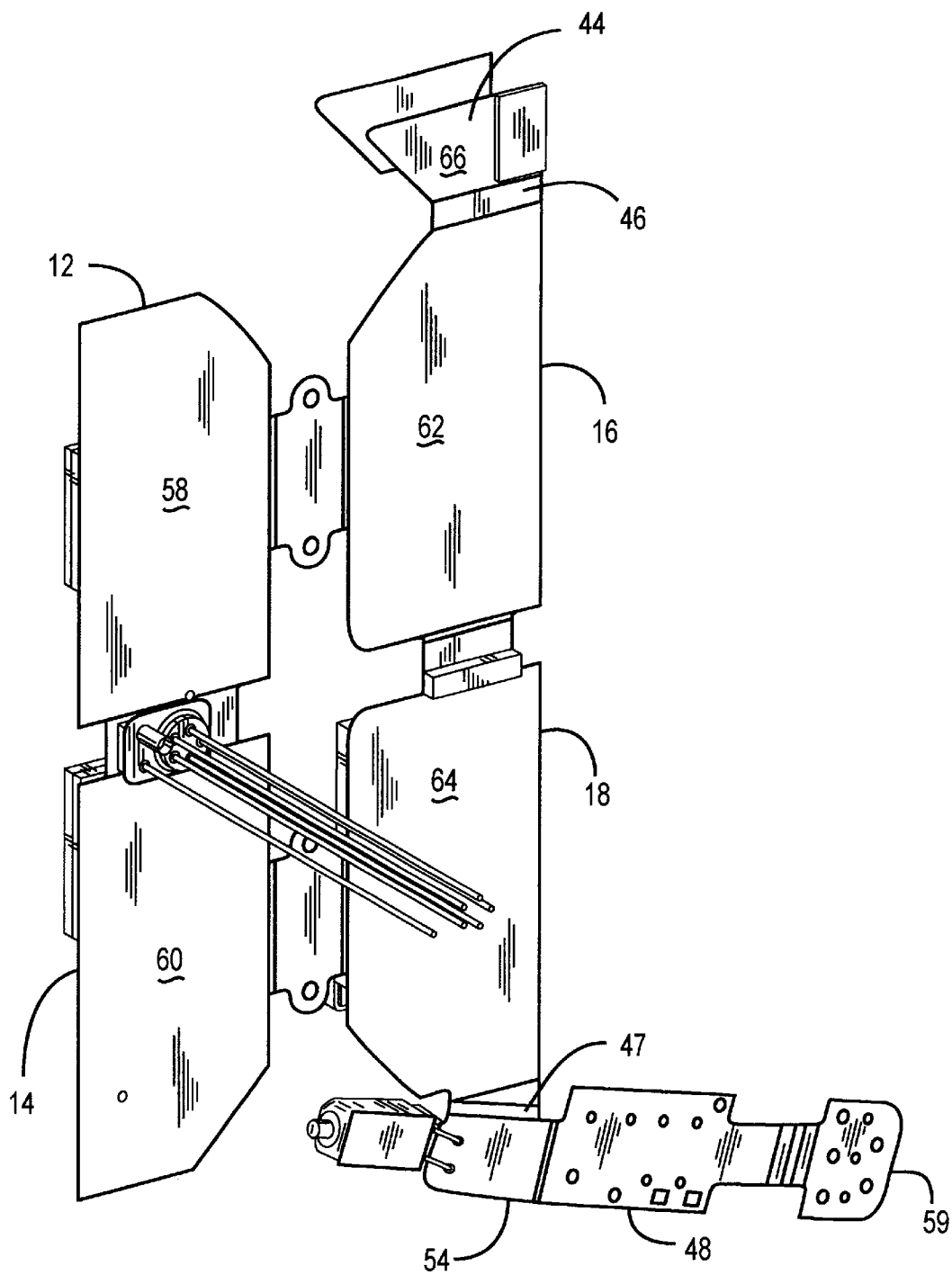
FIG. 2 is a back isometric view of the printed circuit assembly of FIG. 1.

Referring to FIG. 2, there is shown the reverse side of the interconnected circuit panels illustrated in FIG. 1. The circuit panels 12, 14, 16, 18 and 44 include conductive ground planes serving as shield members 58, 60, 62, 64 and 66, respectively.

Figure 3:
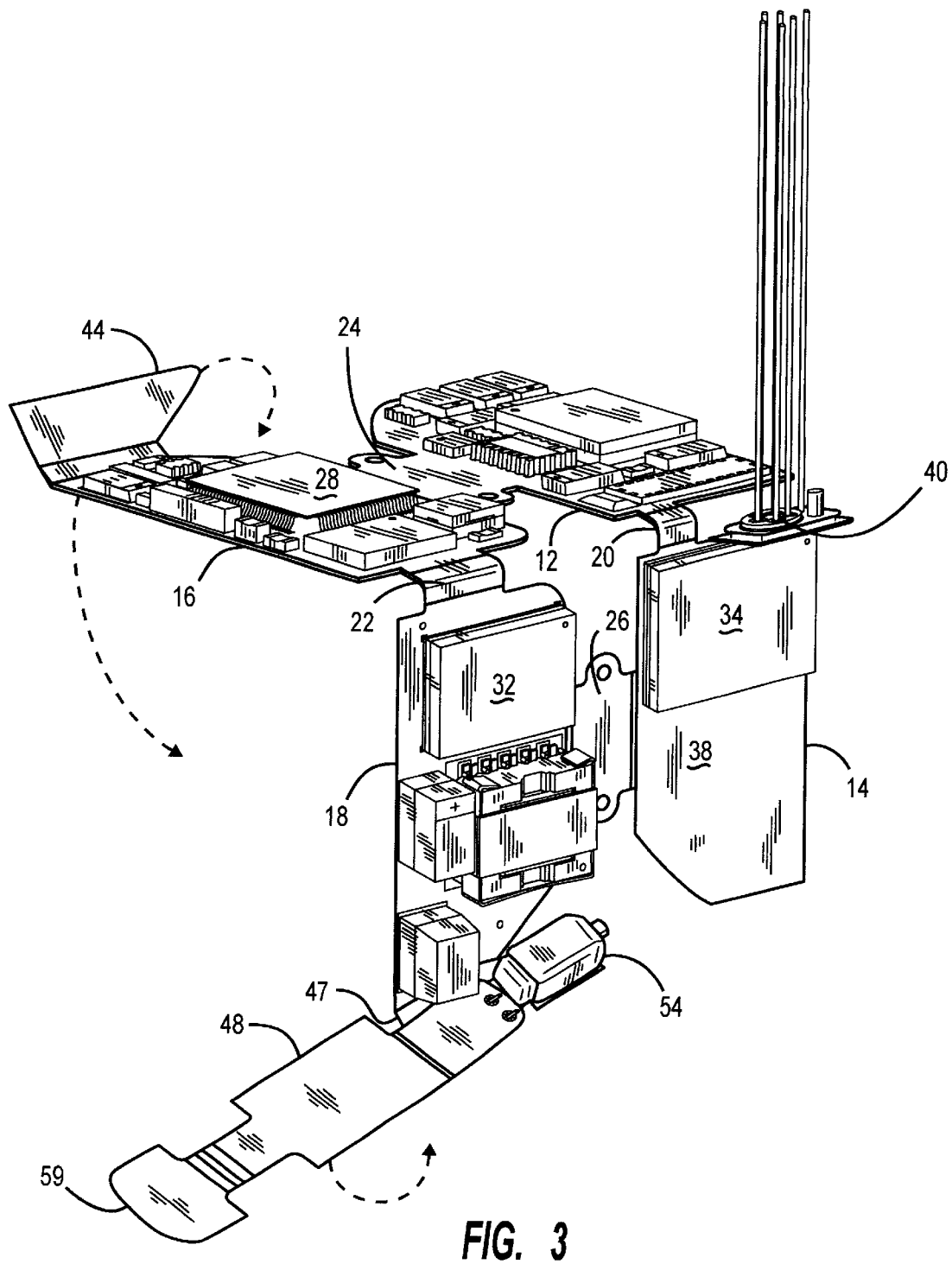
FIG. 3 is an isometric view of the assembly of FIG. 1 when being folded in half.

Referring next to FIG. 3, it shows the circuit assembly 10 in the process of being folded through the flexible flat cable segments 20 and 22 so that the printed circuit panels 12 and 16 are juxtaposed in side-by-side relationship to the panels 14 and 18. When so-folded, the active and passive circuit components visible in the view of FIG. 1 face away from one another and are effectively separated by conductive ground plane shield elements 58, 60, 62 and 64.

Figure 4:
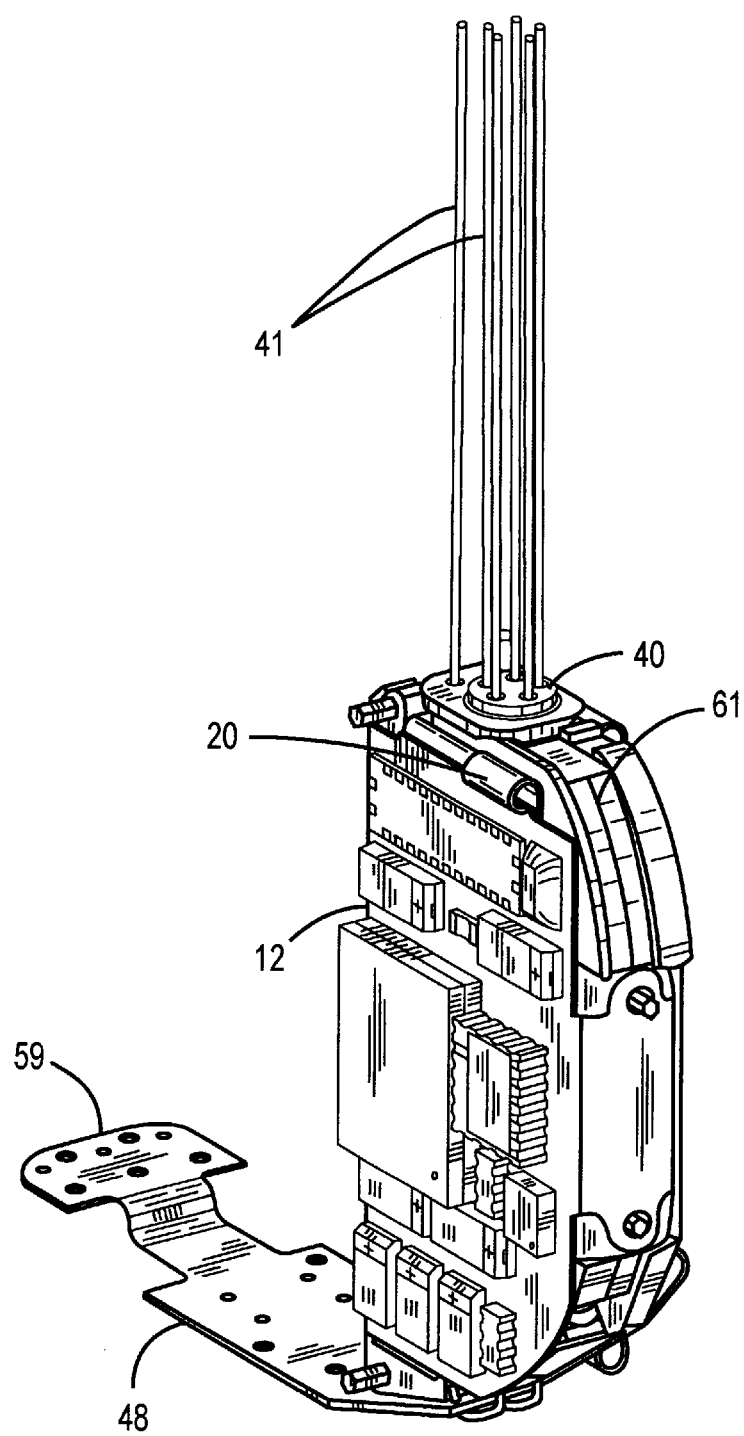
FIG. 4 is an isometric view of the circuit assembly of FIG. 1 in its fully folded state.
Figure 5:
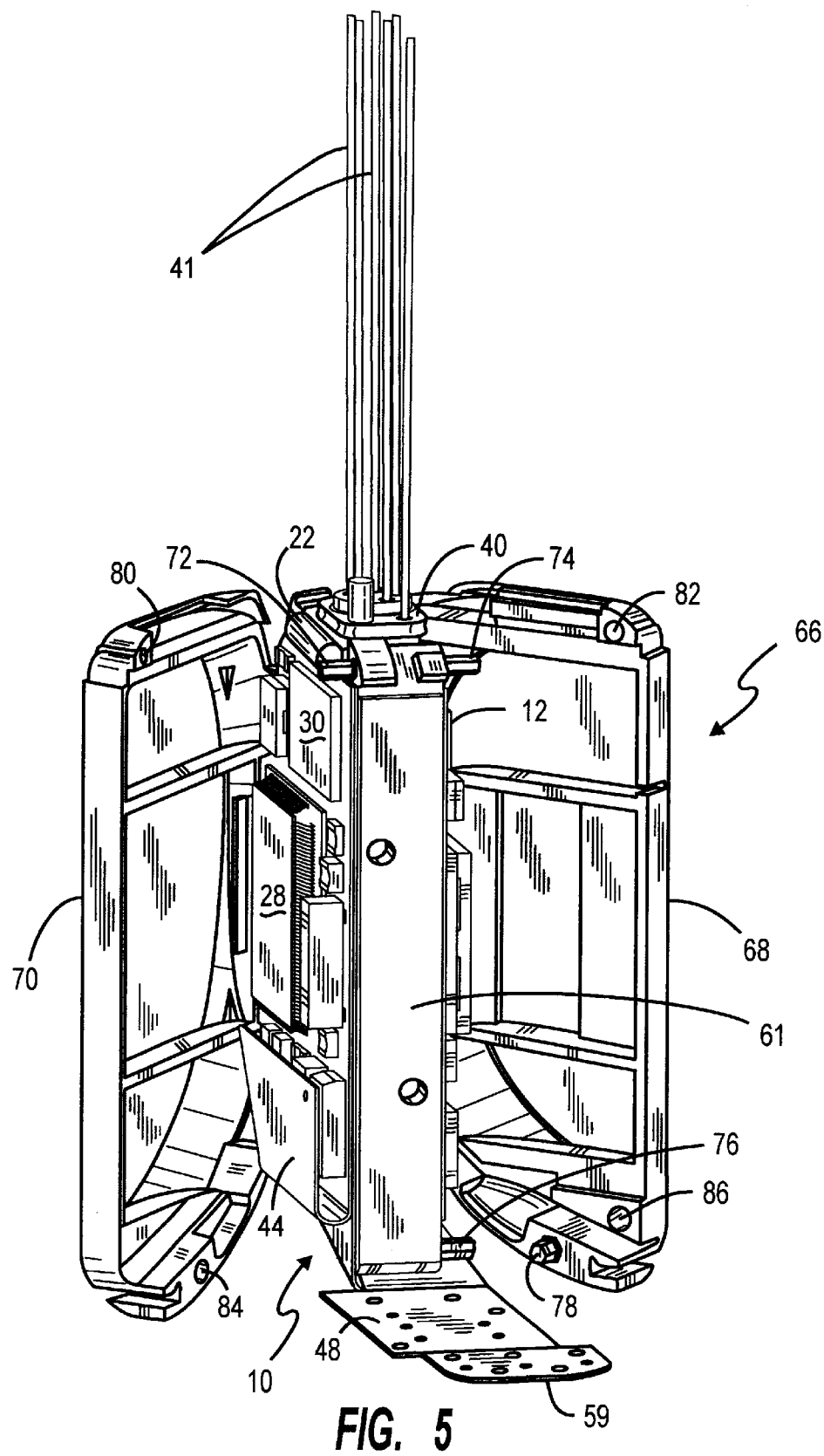
FIG. 5 is an isometric view of the assembly of FIG. 4 inserted in a retainer.

FIG. 4 shows the circuit assembly 10 after it has again been folded, this time by folding flat conductor cable segments 24 and 26, thereby placing the several panels in a substantially parallel, stacked orientation relative to one another. The four panels 12, 14, 16 and 18 with the electronic components in place form a 2×2 matrix when unfolded and a 1×4 stack when the cabling is folded in the manner shown. To maintain the circuit assembly in its fully folded configuration, it may be placed around an inner liner 61 in a basket retainer member as is illustrated in FIG. 5. The retainer is indicated generally by numeral 66 and comprises a pair of molded plastic side members 68 and 70 which are hinged together along a back binding (not shown) that allows the first and second halves 68 and 70 to close about the folded circuit assembly 10. Upper and lower pegs 72–74 and 76–78 on the inner liner and basket retain are adapted to fit within holes 80–82 and 84–86 with a predetermined friction fit to thereby clamp the folded circuit assembly 10 between the retainer halves 68 and 70.

From what is depicted in the drawings and described herein, those skilled in the art will appreciate that the folded construction of the final assembly illustrated in FIG. 5 exchanges surface area for depth and permits economical planar construction of relatively dense electronics on a printed wiring board. In that the components themselves reside only on one surface of the unfolded assembly, conventional pick-and-place machines can be used to position the components onto the substrate as soldered connections between the components and the printed wiring terminal points on the substrates is effected. The flexible junctions between the several panels vary in the number of conductive layers used to accommodate the various signals exchanged between panels, while permitting the inclusion of electrical shield layers to protect signal integrity.

The use of auxiliary panels as low profile integrated shields permits noisy and sensitive circuits to be placed in close proximity without interference. The integrated nature of these shields reduces the number of manufacturing steps and final assembly costs.

As explained, auxiliary components, such as batteries and high voltage capacitors are adapted to be connected directly to the folded assembly, further reducing the interconnect complexity of the device and simplifying the manufacture of the device in question. The flat manufacturing configuration also permits ease of testing due to reduced fixture density and complexity. Once folded, however, the structure becomes very compact and can be readily fitted within the outer housing of the implantable device. By beveling one corner of each of the panels 12, 14, 16 and 18 (as best seen in FIG. 1), when the configuration is in its fully folded condition as illustrated in FIGS. 4 and 5, the resulting folded package is made to better conform to the profile of the housing in which the folded package is fitted.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A circuit assembly comprising:
   at least four printed circuit panels having active and passive circuit components mounted thereon, the four panels being interconnected by flexible flat cabling to form a two by two matrix when the flexible flat cabling is unfolded and the four panels being arranged in a one by four stack when the flexible flat cabling is folded.

2. The circuit assembly as in claim 1 wherein the circuit panels further comprise a conductive ground plane shield configured to prevent electrical interference between the circuit panels when stacked.

3. The circuit assembly of claim 2 and further including terminals coupled to the flexible, flat cabling to which electrical power is adapted to be applied.

4. The circuit assembly of claim 3 and further including a test point panel interconnected to at least one of said four printed circuit panels with flexible, flat cabling.

5. The circuit assembly as in claim 4 wherein the circuit panels further comprise a conductive ground plane shield configured to prevent electrical interference between the circuit panels when stacked.

6. The circuit assembly as in claim 3 wherein the at least four printed circuit panels are generally rectangular and of substantially equal area.

7. The circuit assembly of claim 3 and further including a molded plastic retainer adapted to receive the one by four stacks therein for retaining the stack in a folded state.

8. A method for producing a compact electronic circuit assembly for use in an implantable medical device, comprising the steps of:

(a) forming a printed circuit substrate comprising a plurality of panels, each panel having first and second major surfaces with a pattern of metallization thereon, the plurality of panels being interconnected by flexible printed circuitry links;

(b) populating the plurality of panels on the first major surface thereof with active and passive circuit components;

(c) folding the printed circuit substrate through the flexible printed circuitry links along a first fold line such that the second major surfaces of predetermined ones of the plurality of panels are juxtaposed in face-to-face relation; and (d) following step (c), folding the printed circuit substrate through the flexible circuitry links along a second fold line that extends transverse to the first fold line to thereby place the plurality of panels in a stacked relationship.

9. The method of claim 8 and further including the step of:

(a) providing a retainer member; and (b) placing the printed circuit substrate with the plurality of panels in stacked relationship into the retainer member.

10. The method of claim 8 wherein each of the panels includes a conductive shielding layer and the steps of folding the substrate along the first and second fold lines positions the conductive shielding layer between circuit components on separate ones of the plurality of panels.

* * * * *